United States Patent [19]

Johnson et al.

[11] 4,287,368

[45] Sep. 1, 1981

[54] METHOD FOR PREPARING VANILLIN AND COMPOSITION THEREFOR

[75] Inventors: Garland A. Johnson, Charleston Township, Kalamazoo County; Jacob D. Peuler, Kalamazoo, both of Mich.

[73] Assignee: The Upjohn Company, Kalamazoo, Mich.

[21] Appl. No.: 124,825

[22] Filed: Feb. 26, 1980

Related U.S. Application Data

[62] Division of Ser. No. 950,863, Oct. 12, 1978, Pat. No. 4,242,222, which is a division of Ser. No. 681,999, Apr. 30, 1976, abandoned.

[51] Int. Cl.³ .............................................. C07C 45/30
[52] U.S. Cl. .............................. 568/436; 252/187 R; 252/188.3 R; 424/1.5
[58] Field of Search ................... 568/436; 252/187 R, 252/188.3 R; 424/1.5

[56] References Cited

PUBLICATIONS

Coyle et al., Chem. Abs., vol. 79, (1973), 63924f.
Passon et al., Chem. Abs., vol. 78, (1973), 68940x.
Coyle et al., J. Neurochemistry, (1973), 21(1), 61–67.
Passon et al., Anal. Biochem., (1973), 51(2), 618–631.

*Primary Examiner*—Bernard Helfin
*Attorney, Agent, or Firm*—L. Ruth Hattan; Martin B. Barancik

[57] ABSTRACT

A new radioenzymatic assay for catecholamines utilizing the catechol-0-methyl transferase transfer of a methyl group from a labeled methyl donor to the catecholamines followed by isolation of the 0-methylated($^3$H)catecholamine and the subsequent measurement of radioactivity.

4 Claims, No Drawings

METHOD FOR PREPARING VANILLIN AND COMPOSITION THEREFOR

This is a division of co-pending Ser. No. 950,863 filed Oct. 12, 1978 and now U.S. Pat. No. 4,242,222 which is a division of Ser. No. 681,999, filed Apr. 30, 1976, now abandoned.

BACKGROUND OF THE INVENTION

Diagnostic tests have become an indispensible tool of a physician's armamentarium. Accompanying many diseases and conditions are subtle changes in the body's physiology, particularly in concentrations of compounds associated with the condition. The catecholamines are a group of these compounds. They are identified by the catechol nucleus

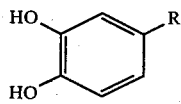

FIG. 1 wherein R is the amine function of the particular compound. The significant catecholamines found naturally in the body are epinephrine, R is

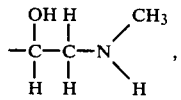

hereafter referred to as E; norepinephrine,

R is 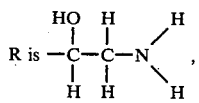

hereafter referred to as NE: and dopamine, R is $-CH_2CH_2MH_2$, hereafter referred to as DA. These catecholamines are found in various tissues of the body, including, inter alia, blood, urine, cerebrospinal fluid, and brain tissue. The quantities of these compounds are extremely small. For example, in blood serum E and NE are present in picogram ($10^{-12}$) quantities.

In recent years there has been substantial interest in measuring catecholamine levels in mammalian systems. Catecholamine levels are significantly increased when pheochromocytomas are present. The catecholamine levels are influenced by the presence of other tumors, such as neuroblastoma, which affect the central nervous system. Knowledge of catecholamine levels is of significance in the diagnosis and management of hypertension, coronary disease, angina pectoris, acute myocardial infarction, and diabetes mellitus.

An early method for measuring catecholamine levels in mammalian systems which was sufficiently sensitive to reach the submicrogram range was the spectrofluorimetric assay of Von Euler and Floding (*Acta Physiol. Scan.* 33: Suppl. 118, 45, 1955). This assay was based on the oxidation of NE and/or E with ferricyanide or iodine to the corresponding trihydroxyindole which in alkaline solution yields a highly fluorescent noradrenolutine or adrenolutine. NE or E must be first isolated from the mammalian system, for example, blood serum or plasma, the supernatant of deproteinized tissue homogenate or cerebrospinal fluid, before the assay can be done. DA is oxidized by iodine to form a dihydroxyindole. The fluorophore produced by this derivative is different from that of NE or E and is the basis for the fluorimetric assay (Carlson and Waldeck, *Acta Physiol. Scand.* 44: 293, 1958). As with NE and E, DA must also be isolated from the mammalian system prior to the assay.

Isolation of the cotecholamines from the superratant of deproteinized tissue homogenate, the blood plasma or the biological fluid is generally done by one of two techniques. The first and most widely used isolation technique is the adsorption of catecholamines onto neutral alumina at pH 8.4-8.6. Catechol containing compounds are adsorbed by alumina and catechol compounds from the mixture are discarded. Catecholes are removed from the alumina by acid elution.

The second isolation technique employs cation exchange chromatography. Due to the ionization of these amines at acidic pH, ME, E and DA can be bound to the exchange resin and then eluted preferentially by increasing acid strength.

Both of these isolation processes are quite lengthy and generally do not yield fractions which are specific for a particular catecholamine. Moreover, the spectrofluorimetric assay systems are relatively insensitive for the needs of the investigator. For NE and E a sensitivity of approximately 50–500 nanograms is obtained. Although refinement of this method has led to techniques that are sensitive to quantities as small as 2 to 3 nanograms, the accuracy of assays at this level of sensitivity are poor, see Engelman et al. *Am. J. Med. Sci.*, 255, 259 (1962). The sensitivity of DA is approximtely 500 nanograms. Even though this assay is relatively insensitive, all the commercial laboratories but one use the spectrofluorimetric assay or some adaptation of it for measuring catecholamines.

Another method of commercially measuring catecholamine levels is potentially available. The enzyme catechol-O-methyl transferase, initially reported and characterized by Axelrod and Tomchick, *J. Biol. Chem.*, 233, 702, 1958, and hereafter referred to as COMT, is an enzyme which transfers a methyl group from a donor molecule to a catechol nucleus thereby forming a 3-methoxy moiety depicted below in FIG. 2 wherein R is the amine functionality.

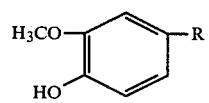

FIG. 2

Later investigators using radiotracers and other techniques including chromatography have related the radiolabeled quantities of metanephrine, hereafter referred to as MM, normetanephrine, hereafter referred to as MMM and methoxytyramine, hereafter referred to as MEOT to the initial quantities of E, NE and DA in the mammalian system. The chemical structures of MM, MMM, and MEOT are shown in FIG. 3.

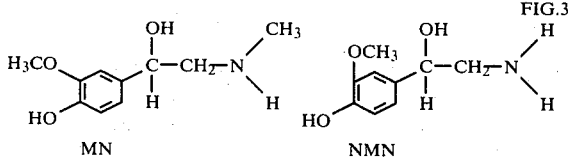

FIG. 3

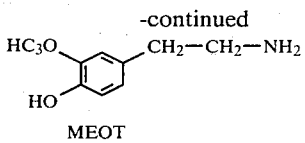

MEOT

In 1968 Engelman, et al., *Am. J. Med. Sci.* 255, 259 (1968) utilized the double isotope dilution derivative technique with COMT to assay for catecholamines, i.e., epinephrine and norepinephrine, in biological specimens. An internal tracer, 7-$H^3$-norepinephrine was employed with the methyl donor S-adenosyl-L-methioninemethyl-$^{14}C$. Prior to assay the urine and blood samples were pretreated to separate the catecholamines. The urine was chromatographed over alumina and the blood sample chromatographed over a cation-exchange resin. After incubation of the chromatographed samples in the enzymatic system, the incubation was stopped and the resulting solution treated and chromatographed over a cation exchange resin. The methanephrines were eluted and oxidized to vanillin with periodate. The vanillin was extracted, purified and counted in a liquid scintillation medium. The typical complex double isotope measurement and calculation was required to find the quantity of catecholamine present.

Engelman followed up his earlier work with another publication, Engelman et al., *Circulation Research*, 26, 53 (1970). Modification of his earlier work now allowed the differential measurement of E and NE in the same sample of 5 to 10 ml. human blood plasma. The same double isotope technique was employed as in the previous publication except that the MM and MMM are separated with thin layer chromatography. Tritium labeled tracer quantities of both E and NE were added along with 100 μg. of both MM and MMM. Prior to assaying, both plasma and urine samples were chromatographed over cation exchange resins. Ethylenediaminetetraacetic acid was added to the plasma sample prior to the chromatographic step. The sensitivity of the assay, as measured by the value which is twice that of the blank, was 250 picograms. Plasma E values cannot be measured very accurately at the lower end of the normal range.

In Passon and Peuler, *Analytical Biochemistry*, 51, 618, (1973) E and NE were assayed using COMT, followed by separation of MM and MMM by chromatography, and thereafter oxidation to vanillin. The blood serum or plasma was used directly without any prior chromatography. Only a single isotope, S-adenosyl-methionine($^3H$)methyl was used. The tritiated methyl donor was diluted with cold methyl donor. Tracer labeled $^{14}C$ compounds were tried but were not helpful in reducing problems such as an accurate estimate of recovery of the catecholamine substrate. At concentrations below 10 μM of cold S-adenosylmethionine, the blank increased substantially. Assay techniques were otherwise similar to those used by Engelman, et al. and others. The sensitivity of the assay was 170 pg. for NE and E, thereby allegedly allowing the measurement of NE and E in less than 1 ml. of human serum.

Coyle and Henry, *J. of Neurochemistry*, 21, 61 (1973) separatednorepinephrine from dopamine in deproteinized brain tissue homogenates by using COMT and S-adenosyl-methionine($^3H$)methyl. After the addition of non-radioactive carrier quantities of MMM and MEOT, the incubate was extracted by an organic solution and the extract repartitioned into aqueous hydrochloric acid. The aqueous phase was washed with the organic solvent. Vanillin-($^3H$) was produced by periodate cleavage $^3H$ MMM. The vanillin-($^3H$) was extracted into an organic solvent and eventually counted in a liquid scintillation medium. The MEOT was extracted from the aqueous periodate phase with a borate buffer and a 3:2 (v/v) toluene-isoamyl alcohol solvent system and counted with a liquid scintillator.

Christensen, *Scand. J. Clin. Lab. Invest.* 31, 343 (1973) determined the level of DA in plasma by a double isotope technique utilizing the COMT procedure. Prior to the enzymatic methyl transfer, the catecholamines were isolated from plasma utilizing aluminum. The COMT and the sample were incubated with S-adenosylmethioninemethyl ($^{14}C$) and tracer quantities of tritium labeled DA. After oxidation of MM and MMM with periodate to vanillin, the MEOT is separated and analyzed in a liquid scintillator. The DA concentration was calculated on a computer from the counts of $^{14}C$ and $^3H$.

Cuello et al. in 1973 analyzed deproteinized brain tissue extracts for DA in the presence of NE. COMT and tritium labeled S-adenosylmethionine were mixed with cold S-adenosylmethionine or $^{14}C$ S-adenosylmethionine. After extracting the incubate with an organic solvent, the organic solvent is back extracted into hydrochloric acid and then chromatographed.

In 1975, Yamaguchi et al., *Circulation Research*, 36, 662 (1975) assayed for endogenous catecholamines in blood with ethylene glycol bis-(aminoethyl ether)-N,N'-tetraacetic acid (hereafter referred to as EGTA) present in the incubation mixture.

Champlain et al., *Circulation Research*, 38, 109 (1976) disclosed that calcium ion was known to inhibit the reaction of COMT from work done by Axelrod and Tomchik. EGTA is a selective chelator of calcium as opposed to magnesium and restores the activity of the enzyme. However, a later publication, Weinshilbaum, et al., *Biochemical Pharmacology*, 25, 573 (1976) states that the possibility that other cations might inhibit the COMT reaction in the presence of optimal concentration of magnesium had not been studied to date.

A new system for assaying catecholamines has now been developed, utilizing the basic COMT system of the past. Catecholamines content of mammalian systems can now be assayed to a sensitivity of 5 picograms for NE and E and 12 picograms for DA. The assay is precise and unusually selective. Furthermore, the assay can be performed rapidly by laboratory personnel having minimal advanced technical training. The assay is presently being used on a successful commercial basis by The Laboratory Procedures Division of The Upjohn Company.

BRIEF DESCRIPTION OF THE INVENTION

In accordance with this invention there is a method for analyzing undifferentiated endogenous epinephrine and norepinephrine levels in a mammalian system selected from the group consisting of the supernatant of the deproteinized tissue homogenate, blood plasma and serum, and biological fluid which comprises a. bringing together an aliquot of the supernatant of the deproteinized tissue homogenate, blood serum or plasma, or biological fluid, with the enzyme catechol-O-methyl transferase, the tritium labeled methyl donor S-adenosyl-L-methionine($^3H$)methyl substantially free of unlabeled methyl donor, a cation of oxidation number +2 which allows the methyl transfer to proceed, a compound which stabilizes the enzyme-substrate system, and an agent which preferentially removes calcium ions from interference with the enzymatic reaction, b. incubating together the components of "a" for a time, temperature and pH sufficient to O-methylate ($^3$H) substantially all of the epinephrine and norepinephrine;

c. extracting the O-methylated ($^3$H) epinephrine and norepinephrine with an organic solvent in which the O-methylated ($^3$H) epinephrine and norepinephrine are preferentially soluble;

d. repartitioning the O-methylated ($^3$H) epinephrine and norepinephrine into an aqueous acid of sufficient strength to protonate the amine;

e. oxidizing O-methylated ($^3$H) epinephrine and norepinephrine to vanillin-$^3$H.

f. extracting vanillin-$^3$H from the aqueous solution with an organic solvent in which the vanillin-$^3$H is preferentially soluble, and g. counting the radiation emitted from the vanillin-$^3$H.

A further aspect of the invention is the method for differentially analyzing the levels of epinephrine and/or norepinephrine obtained from a mammalian system selected from the group consisting of the supernatant of deproteinized tissue homogenate, blood serum or plasma, and biological fluid which comprises performing the same assay steps as above with the additional step of separating the O-methylated epinephrine and O-methylated norepinephrine by chromatographic means. This separation step is performed after the repartitioning and before the oxidation of O-methylated ($^3$H) epinephrine and/or norepinephrine to vanillin-$^3$H.

Another aspect of the invention is the method for assaying the levels of dopamine present in the sample. In the undifferentiated epinephrine and norepinephrine assay, the aqueous oxidation phase remaining after the vanillin extraction is extracted at a basic pH with an organic solvent and the MEOT ($^3$H) counted. In the differential assay for epinephrine and norepinephrine, the dopamine is analyzed in the same manner as in the undifferential assay when the solvent system used to separate the O-methylated ($^3$H) epinephrine and O-methylated ($^3$H) norepinephrine is acidic. If the solvent system for separating the O-methylated ($^3$H) epinephrine from the O-methylated ($^3$H) norepinephrine is basic, the $^3$H MEOT is also separated in the chromatographic system. The $^3$H MEOT is eluted and counted.

Another aspect of the invention is the use of an agent to selectively remove calcium ions from interference with the COMT enzymatic reaction.

A further aspect of the invention is a method for increasing the intrinsic activity of COMT by using EGTA in combination with COMT.

Another aspect of the invention is a method for purifying rat liver COMT utilizing a further ammonium sulfate fractionation. A new COMT composition resulting from this purification is a further aspect of the invention.

A still further aspect of the invention is the purification of vanillin-$^3$H in a scintillation vial employing an acid wash and a method for assaying the radioactivity in such a vial.

Another aspect of the invention is the oxidation of metanephrine-$^3$H or normetanephrine-$^3$H to vanillin-$^3$H with periodate in the presence of silica gel and the composition comprising those components.

A further aspect of the invention is a new basic solvent system used for thin layer chromatography.

Another aspect of the invention is the presence of an aromatic L-amino acid decarboxylase, particularly DOPA decarboxylase, inhibitor in the incubate. A compound of this type inhibits the production of dopamine during this incubation period.

A further broad aspect of the invention is the assemblage of the essential components of the assay into a kit which may be used by laboratories.

Other aspects of the invention will become clear as the description of the invention continues.

DETAILED DESCRIPTION OF THE INVENTION

The catecholamines are found throughout various mammalian systems. As stated previously, these compounds have in common the catechol nucleus and an amine function. Examples of various mammals in which catecholamines can be assayed include human, horse, cattle, dog, cat, rat, mouse, rabbit, and other animals generally used in scientific laboratories for the study of circulatory and myocardial problems. Catecholamines are found in various systems throughout the mammal. Circulating levels of catecholamines are found in the blood. Other biological fluids in the body, for example, urine, cerebrospinal fluid and lymphatic fluids also have significant levels of catecholamine. Tissue samples which can be employed in the assay system is any tissue with sympathetic innervation, such as vascular tissue, liver, adrenal and kidney; brain tissue; tumor containing tissue and the like. When tissue is being assayed, the sample is broken down by any common technique such as homogenizing, tissue press under pressure, and sonication. It is the supernate of this homogenate which is then employed in the assay. In order to maintain the integrity of the system, an acidic pH should be employed. When liquid systems such as blood fractions or other biological fluids are being employed, no preliminary isolation such as alumina or cation exchange chromatography need be employed. Rather the fluid sample per se can be employed.

The size of the sample to be assayed varies substantially depending upon the quantities of catecholamines present. Because of the sensitivity of the assay, blood serum or plasma samples as low as 10 µl. or even less may be readily assayed. Urine samples generally have to be diluted since the quantities of catecholamines present in urine are significantly higher than in blood samples. It should also be noted that tissue samples containing phenochromocytoma will have significantly higher catecholamine levels. The upper level of the volume of the mammalian system being assayed can go as high as one milliliter, if desired. The volume levels required are generally so minute that small laboratory animals can be readily assayed without significant problems. The quantity of catecholamine present in each sample aliquot can vary from about 20 to about 10,000 picograms of E or NE for the undifferentiated assay and from about 3 to about 5,000 for the differential assay for E, NE, and DA. Depending upon the picogram concentration, a general sample aliquot of the system to be assayed is from about 10 to about 50 µl.

As noted previously, COMT is an enzyme which has a general activity for the O-methylation of a catechol nucleus. Although the assay methodology disclosed in this invention is quite specific for endogenous catecholamines, it does not differentiate catechol nuclei from other sources. For example, many drugs administered to mammals, specifically humans, have catechol nuclei or are precursors of metabolites having catechol nuclei. Illustrative examples of such drugs and/or metabolites are α-methyl norepinephrine, α-methyldopamine, isoproterenol, α-methyldopa, and other like compounds. If a mammal has received such drug treatment, the results of this assay utilizing COMT would be unduly high. Consequently, mammals receiving such compounds are inappropriate subjects for this assay.

The enzyme COMT is found in a wide variety of mammals. Examples of such mammals include rat, cow, pig, mouse, guinea pig, cat, rabbit and man. The enzyme is widely dispersed throughout the systems, for examples, liver, kidney, spleen, small intestine, brain the like. The preferred species is the rat. The preferred organ from which the enzyme is isolated is the liver. The methods of isolation are known throughout the art. The usual steps are followed in isolating the enzyme, with the exception that a further ammonium sulfate fractionation is employed. This step, not heretofore practiced in the art, involves resuspending the 30-50 or 55% ammonium sulfate precipitate in a 55% saturated ammonium sulfate solution, separating the phases and proceeding with the usual isolation steps. The addition of this extra fractionation step brings about a substantial reduction in the blank value.

S-adenosyl-L-methionine-($^3$H) methyl is the labeled methyl donor employed in the enzymatic O-methylation. This tritium labeled methyl donor can be made by art known radiochemical methods and is commercially available from New England Nuclear Corp. and Amersham-Searle. The tritium label is at the methyl position. It has now been found that this methyl donor should be present in the incubation mixture at a concentration $\geq$ about 4 μM for maximal activity and maintenance of the catecholamines as the rate determining concentration in the O-methylation. In order to produce the excellent sensitivity of this assay, the labeled methyl donor is essentially free of unlabeled, cold methyl donor S-adenosyl-L-methionines. The addition of unlabeled cold methyl donor makes the assay less sensitive to the catecholamines. If a less sensitive assay is desired, this may be achieved by adding unlabeled, cold S-adenosyl-L-methionine to the assay incubate. The tritium labeled S-adenosyl-L-methionine-($^3$H) methyl should be prepared with maximum radioactivity for maximum sensitivity of the assay. Radioactivity greater than or equal to 8 Ci/mmol can be employed. Preferred radioactivity is from about 10 to about 15 Ci/mmol.

In order for the enzymatic system to be active, at least one of a number of cations of oxidation number +2 must be present in the incubate. Cations of oxidation number +2 which can be used are magnesium, cobalt, and manganese. Magnesium is preferred. The metal can be present as a salt, for example, magnesium chloride. A concentration of cation of from about 10 to about 100 mM, preferably about 25 to about 35 mM, is present in the incubation mixture.

Also present in the incubate is a compound which stabilizes the enzyme-substrate system. This compound maintains the integrity of the system by preventing oxidation of the catecholamines and assists in the continued activity of the enzyme during the incubation. Compounds which can be effectively employed to stabilize the enzyme-substrate system are glutathione, dithiothreitol, ascorbic acid, sodium metabisulfite, mercaptoethanol, cysteine, and the like. Glutathione is preferred. Concentration of the stabilizer in the incubate is from about 1 to about 10 mM, preferably about 2 to about 4 mM. When ascorbic acid is employed, care must be taken to avoid an excess since an inhibition of enzymatic activity can occur.

A further component of the incubate is an agent which preferentially removes calcium ions from interference with the enzymatic conversion. Calcium ions in the presence of activator ions such as magnesium, cobalt or manganese inhibit the enzymatic O-methylation. Consequently, it is extremely advantageous to have present in the incubate an agent which selectively removes calcium ions instead of activator ions from participation in the enzymatic conversion. Agents which accomplish this function are illustratively EGTA, Chelax ®, a resinous substance obtainable from Biorad Laboratories, sodium oxalate, dyes which chelate calcium ion selectively, for example, Murexide ®, and other like agents. EGTA is preferred. Since the agents may differ in their selectivity for calcium ion with respect to the activator ion, extra activator ion may be needed and should be added if necessary. These agents are present in sufficient quantity so as to allow the enzymatic conversion to proceed as rapidly and as efficiently as possible. For example, concentrations of from about 5 to about 25 mM of EGTA in the incubation mixture can be used.

It has also been found that EGTA brings about an increase in the intrinsic activity of COMT. When added to the blank of the incubate, that is, all components of the incubate but the mammalian system, EGTA brings about an increase in COMT enzymatic activity as measured by the amount of O-methyl($^3$H)catecholamine formed.

All the quantities of the incubate are present in quantities which allow the catecholamine concentration to be the rate limiting factor. The enzyme, methyl donor, cation, stabilizing compound and agent which selectively removes calcium ions are present in quantities in excess of those quantities necessary to bring about the timely conversion of the catecholamines to O-methylated($^3$H)catecholamines. All, or essentially all, of the catecholamines present in the mammalian system to be assayed are converted during the incubation period.

The enzymatic incubation is carried out in standard laboratory equipment for a time and at a pH and temperature which allows the enzymatic conversion to go to completion. The pH of the incubation should be maintained between about 7 and about 10. The preferred pH range is from about 8 to about 9. Buffer solutions which are suitable for the incubation are tris, phosphate, or glycine/NaOH. The temperature of the incubation can be from about 25° C. to about 45° C., preferably from about 35° C. to about 40° C. The incubation is allowed to proceed for a period of from about fifteen minutes to about two hours, preferably from about forty to about sixty minutes.

The incubation is stopped by any of a variety of standard means. For example, the temperature can be lowered or elevated or the pH can be raised or lowered. It is preferred to stop the incubation by a lowering of the temperature and the introduction of a higher pH accompanied by a magnesium, cobalt, or manganese binding agent. If desired for economy, time factors, or personal preference, the incubation need not be stopped before the O-methylated($^3$H)catecholamines are selectively removed from the incubate.

The stopping solution can also contain carrier quantities of MM, MMM and MEOT. Since there is such a small quantity of catecholamines present in the sample, the carrier compounds are advantageously added to facilitate the recognition and partitioning of the sample catecholamines throughout the assay. The carrier compounds are generally present as their hydrochloride acid addition salts since this form of the compound is thought to be more stable. In the succeeding assay step, the free base is formed. The carrier compounds are preferably added in the stopping solution prior to the organic solvent extraction of the incubate, although they can be added to the incubate initially, depending upon the euilibrium in the COMT transfer. If the incubate is not stopped, the carrier quantities of MM, MMM and MEOT should still be added to the incubate prior to the preferential organic solvent. A concentration of carrier of from about 2 to about 4 mM can be employed.

The O-methylated($^3$H)catecholamines are now selectively removed from the incubate by solvent extraction. An organic solvent which extracts the MM, MMM and MEOT from the incubate is employed. It is, of course, preferred to have an organic solvent in which the O-methylated catecholamines are preferentially soluble, that is, leaving as much of the incubate components, side reaction products, and other extraneous matter in the aqueous incubate. Any organic solvent which is substantially immiscible with water can be used. Illustrative examples of organic solvents which can be employed are the higher alcohols such as butanol, isoamyl alcohol, hexanol, esters such as ethyl acetate, ethers such as diethyl ether, tetrahydrofuran, dioxane, aromatics such as benzene, toluene, and the xylenes. Preferred organic solvents are isoamyl alcohol, butanol, toluene, and the xylenes. More preferred are certain mixtures of organic solvents, specifically a 35–75% volume to volume, mixture of toluene:isoamyl alcohol, preferably 50–65% toluene:isoamyl alcohol.

The organic extract of O-methylated($^3$H)catecholamines is now repartitioned into an aqueous acid of sufficient strength to protonate the amine function of the catecholamines. Examples of such acids are formic, acetic, propionic, hydrochloric, sulfuric, phosphoric and the like. When performing the assay for the analysis of total, undifferentiated E and NE, any of these acids can be used. However, when the differential assay for E and NE is performed, it is preferable to use an acid which has a relatively low boiling point and which leaves essentially no residue upon evaporation, for example, formic, acetic and propionic acid, preferably acetic acid. The differential assay requires a chromatographic separation step of MMM from MM. The presence of the acid addition salt of MM or MMM interferes with the separation of MM from MMM and each catecholamine from other constituents of the sample. This repartition can be repeated several times for an increased partitioning effect.

We have found that when the aqueous phase is denser than the organic phase, separation of the two phases is facilitated by freezing the aqueous phase. Freezing shortens the assay time and allows for a cleaner, more precise separation of the organic phase from the aqueous phase.

If the total undifferentiated values for E and NE are desired, the following separation step of MM from MMM is not done. Rather, the aqueous acid extract is preferentially dried down, taken up in basic solution and the MM and MMM oxidized to vanillin.

When the differential assay for E and NE is performed, MM is separated from MMM at this point. The usual means of separating the O-methylated catecholamines is by chromatography, for example, paper and thin layer, preferably thin layer chromatography. The aqueous acid extract containing the O-methylated catecholamines is preferably taken to dryness and then solubilized in an organic solvent such as 95% ethanol. The ethanolic solution is applied to a chromatographic plate covered with a thin layer of adsorbent, for example, siliceous materials. The thickness of the layer of adsorbent is that generally used in the art, for example, 50 to 750$\mu$, preferably 200–300$\mu$. Silica gel is preferred. The solvent system used for the separation can be any of the systems known to separate MM from MMM. However, it is preferred to use with silica gel a solvent system of composition 60 isopropyl alcohol, 20 n-butanol, 19 water, and 1 formic acid, as volume to volume percentages. When using this solvent system, MM has an $R_f$ of about 0.59 and MMM an $R_f$ of about 0.7. The MEOT does not separate from the MMM. The separation of MM from MMM occurs rapidly and distinctly. Another solvent system when used in conjunction with silica gel brings about the separation of MEOT from MMM. The basic solvent system of 6 parts t-amylalcohol:2 parts benzene:3 parts methylamine, volume to volume, brings about a separation on silica gel wherein MEOT is furthest from the origin, MM is closer to the origin, and NMN is closest to the origin. This latter solvent system allows for the ready analysis of DA via the radioemission of the separated MEOT.

The basic solvent system employed in the above thin layer chromatographic step is novel. The essential components of the system are alcohol to methylamine in a ratio of about 1:1 to about 5:1 volume to volume alcohol to methylamine. The methylamine is 40% in water. The alcohol is a higher alcohol such as t-amyl alcohol, i-amylalcohol, n-butanol and the like. A non-polar, lipophilic organic compound may also be present in the solvent system. The presence of such a solvent increases the velocity of migration and spot resolution. It may be present in as high a quantity as is consonant with a one-phase solvent system. Illustrative examples of nonpolar lipophilic organic solvents which can be employed are benzene, toluene, m-xylene and p-xylene.

At this point in the assay, the spot containing MN is eluted from the silica gel with a solvent such as ammonium hydroxide, and then extracted with an organic solvent or organic solvent system as previously disclosed with respect to extracting the incubate.

The radiolabeled compounds are then counted. When using the basic solvent system in the chromatographic separation, the MEOT and NMN can be analyzed in the same manner. However, it is preferred to oxidize the MN and NMN obtained from either the acidic or basic solvent separation system to vanillin. This oxidation gives greater specificity to the assay since only the $\beta$-hydroxy catecholamines are subject to this oxidation. This step separates other labeled catechol nuclei not bearing a $\beta$-hydroxy group. Also, since in the acidic solvent system the NMN and MEOT are not resolved, the oxidation of NMN to vanillin is necessary. When only assaying for total or undifferentiated E and NE, the oxidation is also necessary to separate the MEOT from the MN and NMN.

The oxidation of the $\beta$-hydroxy O-methylated catecholamine is accomplished with standard reagents and conditions. After elution of the MN or NMN from the adsorbent, the MN and NMN is contacted with an oxidizing agent such as sodium metaperiodate at a pH of from about 7 to about 12 at a temperature of from about 0° to about 50° C. for a period of from about two to about thirty minutes. The MN and NMN should be quantitatively oxidized to vanillin. The temperature of the reaction is preferably from about 0° to about 40° C., and the time of the reaction is preferably two to ten minutes.

It now has been found that the periodate oxidation can be carried out in the contact presence of silica gel. This increases the amount of assay sensitivity, accuracy and precision since the oxidation step may now be carried out in a single container. The silica gel band containing MN or NMN is scraped off the plate and placed into a tube, the MN or NMN eluted with a basic solvent such as ammonium hydroxide and sodium metaperiodate added. The oxidation to vanillin occurs smoothly and with no difficulty in the contact presence of silica gel.

The oxidation is completed or stopped. The stopping substituent is generally a glycerol solution. If the pH of the system is not already at or below 7, the pH of the system is reduced to <7 with acid. The nature of the acid employed is not significant. Hydrochloric, sulfuric, phosphoric, formic, acetic or propionic are illustrative of the acids which can be employed.

The vanillin is now extracted into an organic solvent which is substantially immiscible with the aqueous fraction. This organic solvent is preferably relatively non-polar so as to effect a good separation between vanillin and relatively polar side products. Examples of such solvents are illustratively benzene, toluene, m-xylene, p-xylene, ethylbenzene, isopropylbenzene, esters such as ethyl acetate, and isopropylacetate, and ethers such as diethyl ether and 1,4-dioxane. When the aqueous phase is denser than the organic phase, separation of the two phases is facilitated by freezing the aqueous phase and removing the organic phase.

The vanillin-$^3$H is now counted. Although various radioemission counting techniques can be employed, such as planchet counting, a liquid scintillation counting technique is preferred. The particular liquid scintillator employed is not significant as long as it will emit a quantum of light when exposed to a $\beta$-ray emitted from tritium. Examples of suitable scintillators are p-terphenyl; 2,5-diphenyloxazole; 2-phenyl-5-(4-biphenylyl)-1,3,4-oxadiazole, 2,5-bis-2-(5-t-butylbenzoxazolyl)thiophene; 2,5-diphenyl-1,3,4-oxadiazole; 2-(4'-biphenyl)-6-phenyl-benzoxazole; 1,4-bis-2-(5-phenyloxazolyl)benzene. The scintillator is solubilized within an organic solvent, the combination of scintillator and solvent hereafter referred to as the liquid scintillation medium. The organic solvent containing vanillin is added to the liquid scintillation medium and counted. A preferable method of extracting the vanillin-$^3$H is to use the iquid scintillation medium as the extractant. The specificity of the assay can be further improved by contacting the vanillin containing organic solvent with an aqueous acid, thereby removing additional water soluble impurities. Although this extraction can be done prior to the addition of the vanillin containing organic solvent to the liquid scintillation medium, it is preferred to have the aqueous acid phase in contact with the liquid scintillation medium. In this manner, the number of separate transfers and phase separations is minimized. When the vanillin is added to the liquid scintillation medium, the vanillin remains in the organic layer and is counted by the scintillator. However, any tritium labeled contaminant extracted into the aqueous acid phase is not counted since the scintillator is in the organic phase and the tritium emission, $\beta$-ray, is stopped by the aqueous phase and interface. The liquid scintillation medium should be selected so that there is little or no scintillator soluble within the aqueous phase.

If DA is desired to be assayed as well, the pH of the aqueous periodate phase is raised to above 7, preferably 9.8 to 10.1, and MEOT extracted with an organic solvent as used in the vanillin extraction. Counting of the radioactive emissions from MEOT-$^3$H is achieved in a similar manner as to vanillin-$^3$H.

Concurrently with the mammalian system having the unknown catecholamine level, a blank sample having all the incubate components except the mammalian system is assayed in the same manner. The sensitivity of the assay is determined as the level of catecholamine which has double the counts of the blank. The standard curve for the assay is obtained by assaying known quantities of E, NE or DA alongside the unknown and blank. The counts obtained with the known concentration of E, NE, or DA is plotted against the concentration. The unknown concentration of catecholamine is then determined by the number of counts emitted with reference to the standard curve.

In this manner, we have been able to attain sensitivities of 3 pg. for E, 5 pg. for NE, 12 pg, for DA, and 5 pg, for the total undifferentiated E and NE. An accuracy of 5–12% coefficient of variation is obtained from mammalian systems of extremely small sample size. The standard shows first order kinetics for a range of from about 3 to at least 3000 pg. The assay system is versatile, rapid and commercially useful.

Following are specific examples of the assay. The examples are intended to be only illustrative and not limiting of the invention concepts embodied in this patent application.

EXAMPLE 1

A. Preparation of Catechol-O-methyl Transferase

The enzyme preparation generally follows the method of Axelrod and Tomchick, *J. Biol. Chem.* 233, 702, 1958.

Rats are sacrificed. The livers are removed, rinsed in cold isotonic KCl (1.15%) blotted dry, weighed and homogenized in four volumes of isotonic KCl. The homogenate is centrifuged for thirty minutes at 78,000 g. The supernatant is decanted and the pH of this solution is adjusted with stirring to pH 5 with the dropwise addition of 1 N acetic acid. After standing in the cold, this solution is centrifuged to remove the suspension which forms.

The resulting supernatant is decanted and ammonium sulfate (AmSO$_4$) is added slowly to bring the AmSO$_4$ concentration to 30% saturation. After centrifugation the supernatant is decanted and AmSO$_4$ is added to raise the concentration to 55% saturation. The solution is centrifuged to produce the 30–55% AmSO$_4$ fraction.

The 30–55% AmSO$_4$ residue is now dissolved in 1 mM phosphate (PO$_4$) buffer, pH 7.4 containing 0.1 mM dithiothreitol (or 0.2 mM glutathione) and AmSO$_4$ is again added slowly to bring the AmSO$_4$ concentration to 55% of saturation. This additional AmSO$_4$ fractionation provides an enzyme preparation which provides a lower blank. After centrifugation the residue is again dissolved in the above PO$_4$ buffer and dialyzed against 4 changes of the same buffer. This dialysis usually takes 14–18 hours to perform.

The activity of the enzyme preparation is determined and the volume is adjusted for optional use in the catecholamine assay. Protein concentration of the enzyme preparation is also determined.

Due to the presence of aromatic-L-amino acid decarboxylase activity in this preparation, a decarboxylase inhibitor, such as benzyloxyamine hydrochloride or 3-hydroxy-4-bromobenzyloxyamine phosphate, is added into the enzyme preparation at a concentration of $10^{-3}$ M. Incubate inhibitor concentration is $10^{-3}$ to $10^{-5}$ M.

B. Solutions

The following solutions are prepared:

1. Stabilizing Solution—0.5 ml. total volume 10 mM reduced glutathione in 0.01 N HCl 2. Standards Solution—0.5 ml. total volume Norepinephrine, epinephrine and dopamine dissolved in stabilizing solution to final concentration of 100 µg. of each base/ml.

3. Buffer Solution—2 ml. total volume

A solution containing 1000 mM Tris(hydroxymethyl)aminomethane, 100 mM EGTA and 300 mM magnesium chloride.

4. S-Adenosyl-L-methionine-$^3$H methyl—0.4 ml. total volume

Specific activity >8 Ci/mmol and 5 µCi $^3$H/10 µl in dilute sulfuric acid/ethanol.

5. Catechol-O-methyl transferase from rat liver—0.45 ml. total volume

Protein concentration of enzyme solution varies from 15 to 40 mg./ml. Solution also contains phosphate buffer, glutathione and dithiothreitol.

6. Stopping Solution—5 ml. total volume

Contains 800 mM boric acid and 80 mM disodium EDTA in 1 N sodium hydroxide, 4 mM DL-metanephrine HCl, 4 mM DL-normetanephrine HCl, and 4 mM methoxytyramine HCl.

7. Sodium metaperiodate 4% (w/v) solution—5 ml. total volume

8. Glycerol 10% (v/v) solution—5 ml. total volume

C. Preparation of Mammalian System

A sample of human blood is drawn from a patient. The blood is collected into a tube containing a mixture of EGTA (250 mM) and glutathione (200 mM). The solution should have a pH of 5–6. 20 µl. of the solution is added for each ml. of whole blood collected. Plasma is then obtained by centrifugation of the blood sample. The plasma is frozen. Care should be taken to free the sample of fibrin and other particulate matter or cloudiness.

D. Reagent Mixture

A reagent mixture is prepared with the following components from B and in the following order and proportions:

| | |
|---|---|
| Solution 3 | 10 µl. |
| Solution 4 | 10 µl. |
| Solution 5 | 5–20 µl. |
| Distilled Water* to a total volume of | 40 µl. |

*(Deionized, glass distilled)

Vortex the mixture lightly before the enzyme is added and lightly after the reagent mixture is complete. Multiples of the 40 µl. reaction mixture are prepared.

E. Standard and Stabilizing Solution

Dilute an aliquot of Solution 2 in a ratio of 1:10,000 with chilled distilled water and store in an ice bath. This will provide a "working standard" of 100 picograms of each catecholamine per 10 µl.

An aliquot of Solution 1 is similarly diluted.

E. Incubation

To a tube containing 50 µl. of the blood serum is added 10 µl. of Solution 1 and 40 µl. of the reagent mixture of Step D.

A blank, a reference standard, and a plasma sample of known catecholamine concentration is run alongside the unknown samples which are done in duplicate. The reference standard is included to determine the O-methylating efficiency of the enzyme in water and the absence of the mammalian system. The plasma sample of known catecholamines is included to determine the quality control of the assay.

The blank is prepared from 50 µl. of distilled water, 10 µl. of Solution 1 and 40 µl. of the reagent mixture.

The reference standard is prepared from 50 µl. of distilled water, 10 µl. of the working standard of Step E and 40 µl. of the reaction mixture.

The plasma sample of known catecholamine content is prepared from 50 µl. of blood plasma, 10 µl. of working standard of Step E and 40 µl. of the reaction mixture.

The above sample tube containing the unknown and the other solution tubes are treated the same throughout the assay. However, only reference to the unknown sample tube shall be made in the following steps.

The sample tube is vortexed lightly and incubated at 37° C. for sixty (60) minutes in an oscillating water bath. After the incubation the tube is returned to the ice bath and 50 µl. of solution 6 is added.

G. Extraction

Two (2) ml. of toluene:isoamyl alcohol (3:2, volume/volume) are added to the stopped incubate. The mixture is vigorously vortexed and centrifuged (2 minutes at 2,000 rpm). Subsequent centrifugations are done in the same manner. Two distinct layers will result. The tube is placed in a dry ice-ethanol bath and the aqueous layer frozen. The organic phase is decanted into a tube containing 0.1 ml. of 0.1 N acetic acid. The tube and contents are vortexed, centrifuged and frozen in the same manner as before. The organic phase is aspirated from the frozen aqueous phase and discarded. The frozen aqueous phase is thawed, 1 ml. of toluene:isoamyl alcohol (3:2, volume/volume) is added, the tube and contents are vigorously vortexed and centrifuged. The aqueous phase is frozen and the upper organic phase is aspirated and discarded.

H. Separation

All of the acetic acid phase from G is applied to the bottom of a silicagel GF plate 2.5×10 cm, 250 micron layer obtained from Aaltech, Inc. The aqueous spot is dried with the aid of 0.15 ml. of absolute ethanol added to the tube prior to spotting and a warm air flow. The spotted plate is placed in a paper lined preequilibrated thin layer chromatography developing tank. The plates are developed with a solvent system of isopropyl alcohol/n-butyl alcohol/water/formic acid, 60:20:19:1. The solvent is permitted to move to the top of the plate, approximately one hour. Remove the plate and dry thoroughly. The zones are visualized under 254 nm ultraviolet light. The upper zone contains NMN and MEOT. The lower zone contains MN. The silica gel of each zone is scraped off the plate and put into different tubes.

I. Oxidation of NMN

To the tube containing the NMN and MEOT, add 1 ml. of 1 N ammonium hydroxide to elute the amines from the silica gel and vortex vigorously. 50 μl. of Solution 7 is added and the tube vortexed. Four minutes after the addition of Solution 7, add 50 μl. of Solution 8 and vortex.

J. Extraction and Counting of Vanillin from NMN

100 μl. of glacial acetic acid is added to the tube and vortexed. 10 ml. of toluene/Liquifluor ® is added to the tube and the tube vigorously shaken for thirty seconds. The tube is centrifuged for two minutes at 2000 rpm, the layers allowed to separate and the aqueous layer frozen. The upper organic layer is decanted into a separate scintillation vial containing 2 ml. of 0.1 N acetic acid. The vial is capped, shaken vigorously, and counted in a liquid scintillation counter. The radioactivity in the vial comes from the level of NE in the sample.

K. Extraction and Counting of MEOT

The frozen aqueous layer of J is thawed and 5 ml. of toluene is added. The tube and contents is vortexed, centrifuged for two minutes at 2,000 rpm and the aqueous layer frozen. The upper organic phase is aspirated and discarded. 0.3 ml. of concentrated ammonium hydroxide is added and the tube vortexed. The pH of the remaining aqueous phase should be between 9.8 and 10.1. Ten ml. of toluene:isoamyl alcohol (3:2 volume/volume) is added. The tube is vigorously shaken, centrifuged for two minutes at 2,000 rpm and the aqueous layer frozen. The upper organic phase is decanted into a scintillation vial containing 10 ml. of Diotol ®, a liquid scintillation medium obtained from Burdick and Jackson. The vial is shaken and counted in a liquid scintillation counter. The radioactivity in the vial comes from the level of DA in the sample.

L. Oxidation of MN, Extraction and Counting of Vanillin from MN

The scrapings of silicagel of the lower zone are treated in the same manner as in I. The extraction and counting is performed in the same manner as J. The radioactivity in the vial comes from the level of epinephrine in the sample.

EXAMPLE 2

In order to perform the non-differentiated assay for total levels of NE and E, the same assay procedure as in Ex. 1 is done except that the separation step is omitted. The acetic acid phase obtained from the toluene:isoamyl alcohol (3:2, volume/volume) extract of the stopped incubate is dried under a stream of air or reduced pressure. 1 ml. of 1 N ammonium hydroxide is added to the dried residue and the tube and contents vortexed. The contents of the tube are then oxidized to vanillin, extracted and counted as in Steps I and J of Example 1. The radioactivity of the vial comes from the total, undifferentiated levels of epinephrine and NE in the sample.

EXAMPLE 3

The assays of Examples 1 and 2 are performed on human urine samples or the supernatants of deproteinized tissue homogenates.

Similar assay results are obtained as in the above examples.

In order to secure a more reproducible and accurate assay level of dopamine in each of Examples 1, 2 and 3, a DOPA decarboxylase inhibitor is present in the incubation mixture. Compounds which can inhibit the enzyme DOPA decarboxylase are illustratively members of the benzyloxyamine family and water soluble hydrazines. Illustrative examples of the benzyloxyamines are benzyloxyamine, 3-hydroxy-4-bromobenzyloxyamine and their acid addition salts, for example, sulfuric, phosphoric, and hydrochloric. An example of a water soluble hydrazine is phenylhydrazine.

A further broad aspect of the invention is the assemblage of essential components of the assay into a kit utilized in laboratories. As stated previously, knowledge of catecholamine levels are significant in the diagnosis of a number of conditions. Commercial laboratories, hospitals and clinics would have a substantial need for this assay. Such a need could be best filled by having available numerous multiples of the necessary reagents together with the appropriate instructions concerning the assay. Such a kit could be readily available by commercial shipping to satisfy the needs of the laboratories, hospitals and clinics. In accordance with this invention, there is a container having within it a multiplicity of smaller containers and contents, said contents comprising the items enzymes catechol-O-methyl transferase, the labeled methyl donor S-adenosyl-L-methionine($^3$H-)methyl essentially free of unlabeled methyl donor, a cation of oxidation number +2 which allows a catechol-O-methyl transferase catalyzed O-methylation of a catecholamine to proceed, a compound which stabilizes a catechol-O-methyl-transferase-catecholamine enzyme-substrate system, and an agent which selectively removes calcium ions from interference with a catechol-O-methyl transferase catalyzed O-methylation of a catecholamine; with the proviso that the S-adenosyl-L-methionine($^3$H)methyl does not have any other item in its smaller container and with the overall proviso that each item is of such a quantity that the enzyme catalyzed transfer of methyl from the labeled donor to the catecholamine, initiated from the bringing together of all the items at a proper pH and temperature and in the presence of a catecholamine sample from a mammalian system selected from the group consisting of the supernatant of a deproteinized homogenate, blood serum or plasma, and a biological fluid, shall O-methylate ($^3$H) substantially all of the catecholamines in the sample.

The large container which holds the smaller containers can be made of styrofoam or any other material which is reasonably impact resistant. The styrofoam or other material is solid throughout with holes in the top wherein the smaller containers, usually circular vials, will snugly fit. Inside the smaller containers will be contents which will go into the assay incubate. The labeled methyl donor should not have any other item in its container. The enzyme, cation, enzyme-substrate stabilizing compound, and agent which selectively removes calcium ion can each be within its own smaller container or any combination of them within a small container. Other reagents useful in the assay can also be included in the kit, for example, the buffer system being used to maintain the pH of the incubate and the incubate stopping solution. The incubate stopping solution should obviously not be present in any smaller container whose contents have an incubate component. The larger container holding the smaller containers is partially or wholly covered by a top which is free of the container or attached thereto in some manner as by a hinge. Within the container or top or attached to the container or top is a means for providing instructions on the assay procedure. This means can be in the form of a printed sheet, a tape recording, or any other means which conveys the information concerning the proper procedure for performing the assay.

Because of the relatively unstable nature of some of the reagents, the kit should be kept at a reduced temperature when not in use, preferably below −20° C.

It should be noted that the exemplification and preferences which apply to the assay components apply equally as well to the kit components used in the assay.

Throughout the specification and claims is the expression "O-methylated($^3$H)epinephrine and norepinephrine". It is to be understood that the norepinephrine is also O-methylated($^3$H). A similar interpretation is to be understood when the ($^3$H) is not present.

The concentration of enzyme generally used in the incubation is that amount necessary to obtain maximal velocity with a given amount of methyl donor and catecholamine.

Earlier in the specification, the acidic solvent system for chromatographic separation was indicated as being preferred. A new preference has been established for the basic solvent system, specifically 6 parts t-amylalcohol:2 parts benzene; 3 parts methylamine solution, volume to volume.

When dealing with a mammalian tissue sample, the tissue must be disrupted and deproteinized prior to use in the assay. This can be done by means such as homogenizing, sonication or tissue press under pressure. The solid mass is separated from the liquid by centrifugation. The liquid supernatant is employed in the assay. The phrase "supernatant of the deproteinized tissue homogenate" appearing through the specification and claims is intended to mean the supernatant of tissue disrupted by any means, not just a homogenizing technique.

A "tris" buffer is a tris(hydroxymethyl)aminomethane buffer. Such a buffer is used to maintain the pH of the incubate.

When referring throughout the specification to xylenes as a solvent which extracts the O-methylated($^3$H-)catecholamines, o-xylene is intended to be included as well as m- and p-xylene.

Throughout the specification and claims, a component of the assay incubate has been "an agent which preferentially removes calcium ions from interference with the enzymatic reaction". The function of these agents is to stop the calcium ion from inhibiting the enzymatic reaction. Since enzyme activating cations of oxidation number +2 such as magnesium, cobalt and manganese are necessary for enzyme activity, it is of course preferred to have an agent which selectively removes the calcium ion from interference with the enzymatic reaction, such as EGTA, leaving the enzyme activating cation concentrations at a level wherein enzyme activation occurs.

An agent which removes the calcium ion from interference with the enzymatic reaction need not do so preferentially but can still be used in the assay. For example, many chelating agents will remove significant quantities of magnesium as well as calcium and can be used in the assay. The loss of available enzyme activating cation in the incubate can be overcome by the addition of extra activating cation in sufficient quantity to produce substantial or preferentially optimal enzyme activity.

Agents of this "nonselective" type which remove calcium from interference with the enzymatic reaction are illustratively ethylene(dinitrilo)tetraacetic acid (EDTA), usually as the sodium salt; 1,2-diaminocyclohexane N,N,N',N'-tetraacetic acid; and N'(2-hydroxyethyl)ethylene diamine N,N,N'-triacetic acid. The concentration of the agent in the assay is from about 2 to about 50 mM of agent, preferably about 5 to about 20 mM. Ethylene(dinitrilo)tetraacetic acid (EDTA) is the preferred compound of this category. The quantity of excess activating ion concentration needed in the incubate to achieve substantial or maximal enzyme activation can be readily calculated from knowledge of the binding capacity of the particular agent being employed or by simple experimentation.

It is to be understood that this nonselective agent which also removes enzyme activating ions as well as calcium ion from interaction with the enzyme can be substituted for the "agent which preferentially removes calcium ions from interference with the enzymatic reaction" in the assay procedure within the specification and within the claims as well. This substitution can be made in independent claims 1, 23, 63, 64, 93, 101, 121 and 126. As an example of this further aspect of the invention is the composition which comprises the enzyme catechol-O-methyl transferase, a tritium labeled methyl donor S-adenosyl-L-methionine($^3$H)methyl essentially free of unlabeled methyl donor, a cation of oxidation number +2 which allows the methyl transfer to proceed, compound which stabilizes the enzyme-substrate system, an agent which removes calcium ions from interference with the enzymatic reaction and a mammalian system selected from the group consisting of the supernatant of deproteinized tissue homogenate, a blood serum or plasma, and a biological fluid, the transferase, cation, stabilizing compound, methyl donor, and agent which removes calcium ions present in such quantities that substantially all the epinephrine, norepinephrine and dopamine present in the mammalian system are O-methylated-($^3$H).

We claim:

1. A method for oxidizing metanephrine or normetanephrine to vanillin which comprises contacting the metanephrine or normetanephrine with periodate in the contact presence of silica gel.

2. A method in accordance with claim 1 wherein the metanephrine or normetanephrine is tritium labeled at the methoxy position.

3. A composition which comprises a catecholamine selected from the group consisting of metanephrine and normetanephrine, silica gel and periodate.

4. A composition in accordance with claim 3 wherein the catecholamine is tritium labeled at the methyl position.

* * * * *